(12) United States Patent
Chung et al.

(10) Patent No.: US 11,491,482 B2
(45) Date of Patent: Nov. 8, 2022

(54) METHOD FOR EXTRACTING NUCLEIC ACID AND EXTRACTION CASSETTE THEREOF

(71) Applicant: Delta Electronics, Inc., Taoyuan (TW)

(72) Inventors: Wei-Yu Chung, Taoyuan (TW); Song-Bin Huang, Taoyuan (TW); Shing-Lun Liu, Taoyuan (TW); Yu-Kai Kao, Taoyuan (TW); Yi-Chen Li, Taoyuan (TW)

(73) Assignee: DELTA ELECTRONICS, INC., Taoyuan (TW)

( * ) Notice: Subject to any disclaimer, the term of this patent is extended or adjusted under 35 U.S.C. 154(b) by 734 days.

(21) Appl. No.: 16/229,620

(22) Filed: Dec. 21, 2018

(65) Prior Publication Data

US 2019/0111428 A1 Apr. 18, 2019

Related U.S. Application Data

(63) Continuation-in-part of application No. 15/018,067, filed on Feb. 8, 2016, now Pat. No. 10,213,783.
(Continued)

(30) Foreign Application Priority Data

Jul. 17, 2015 (TW) .................................. 104123190
Dec. 14, 2018 (CN) .......................... 201811532891X

(51) Int. Cl.
*B01L 3/00* (2006.01)
*C12N 15/10* (2006.01)
*B01L 7/00* (2006.01)

(52) U.S. Cl.
CPC ........... *B01L 3/502715* (2013.01); *B01L 7/00* (2013.01); *C12N 15/1003* (2013.01);
(Continued)

(58) Field of Classification Search
CPC .. B01L 3/502715; B01L 7/00; B01L 2200/04; B01L 2200/16; B01L 2300/0861;
(Continued)

(56) References Cited

U.S. PATENT DOCUMENTS 7,192,559 B2 3/2007 Chow et al.
2005/0045538 A1 3/2005 Seto et al.
(Continued)

FOREIGN PATENT DOCUMENTS

CN 101765463 A 6/2010
CN 106337015 A 1/2017
(Continued)

OTHER PUBLICATIONS

Partial Search Report of corresponding EP application No. 18215506.9 dated Mar. 11, 2019, 15 pages.
(Continued)

*Primary Examiner* — Benjamin R Whatley
*Assistant Examiner* — Jacqueline Brazin
(74) *Attorney, Agent, or Firm* — Muncy, Geissler, Olds & Lowe, P.C.

(57) ABSTRACT

The present invention provides an extraction cassette, which includes an extraction module and a liquid receiving module. The liquid receiving module communicates with the extraction module. The liquid receiving module includes a receiving module body, a sample compartment, a sealing member, an alcohol compartment and a first path. The receiving module body includes a first side, a second side and a sample feeding hole. The sample compartment is formed on the receiving module body. The sample compartment communicates with the sample feeding hole, the sample compartment includes a first sample compartment connection hole and a second sample compartment connection hole. The sealing member is adapted to seal the sample
(Continued)

feeding hole. The alcohol compartment is formed on the receiving module body. The alcohol compartment communicates with the first sample compartment connection hole of the first sample compartment via the first path.

13 Claims, 16 Drawing Sheets

Related U.S. Application Data

(60) Provisional application No. 62/610,444, filed on Dec. 26, 2017.

(52) U.S. Cl.
CPC ..... *B01L 2200/027* (2013.01); *B01L 2200/04* (2013.01); *B01L 2200/10* (2013.01); *B01L 2200/16* (2013.01); *B01L 2300/0861* (2013.01)

(58) Field of Classification Search
CPC ........... B01L 2200/10; B01L 2200/027; C12N 15/1003
USPC .......................................................... 436/178
See application file for complete search history.

(56) References Cited

U.S. PATENT DOCUMENTS

| | | |
|---|---|---|
| 2005/0142571 A1 | 6/2005 | Parthasarathy et al. |
| 2006/0019379 A1* | 1/2006 | Taylor .................... C12M 47/06 435/306.1 |
| 2006/0110725 A1 | 5/2006 | Lee et al. |
| 2006/0172642 A1 | 8/2006 | Sasaki et al. |
| 2007/0292858 A1* | 12/2007 | Chen ....................... B01L 3/502 422/68.1 |
| 2008/0121591 A1* | 5/2008 | Knight .................... C12M 47/06 436/178 |
| 2008/0213872 A1* | 9/2008 | Regan ..................... G16H 10/40 435/283.1 |
| 2009/0148933 A1 | 6/2009 | Battrell et al. |
| 2010/0216225 A1 | 8/2010 | Dyer et al. |
| 2013/0236375 A1* | 9/2013 | Tan ................... B01L 3/502723 422/502 |
| 2014/0206073 A1* | 7/2014 | Park ....................... C12Q 1/686 435/287.2 |
| 2015/0024436 A1* | 1/2015 | Eberhart ................ B01L 3/527 435/91.2 |
| 2017/0015993 A1 | 1/2017 | Chen et al. |

FOREIGN PATENT DOCUMENTS

| | | |
|---|---|---|
| TW | 201326814 A1 | 7/2013 |
| TW | 201704477 A | 2/2017 |
| WO | WO 2005/073691 A1 | 8/2005 |
| WO | WO 2005/111210 A1 | 11/2005 |
| WO | WO-2005121963 A2 | 12/2005 |
| WO | WO 2006/032044 A2 | 3/2006 |
| WO | WO 2007/149791 A2 | 12/2007 |
| WO | WO 2008/149111 A1 | 12/2008 |
| WO | WO 2010/091080 A2 | 8/2010 |

OTHER PUBLICATIONS

Extended Search Report of corresponding EP application No. 18215506.9 dated Jun. 14, 2019, 13 pages.

Office Action and Search Report of corresponding TW application No. 107145106 dated Oct. 5, 2019, 8 pages.

Office Action of corresponding CN application No. 201811532891.X dated Dec. 28, 2020, 8 pages.

* cited by examiner

METHOD FOR EXTRACTING NUCLEIC ACID AND EXTRACTION CASSETTE THEREOF

CROSS REFERENCE TO RELATED APPLICATIONS

This application claims the benefit of U.S. Provisional Application No. 62/610,444, filed Dec. 26, 2017 the entirety of which is incorporated by reference herein.

This application is a Continuation-In-Part of pending U.S. patent application Ser. No. 15/018,067, filed Feb. 8, 2016 and entitled "Nucleic acid extracting device".

This Application claims priority of China Patent Application No. 201811532891X, filed on Dec. 14, 2018, the entirety of which is incorporated by reference herein.

BACKGROUND OF THE INVENTION

Field of the Invention

The present invention relates to an extraction cassette, and in particular to an extraction cassette with a liquid receiving module.

Description of the Related Art

In a conventional liquid receiving module, the sample compartment typically has a pressure supply opening connected to a pressure source. The movement of the liquid inside the sample compartment can be controlled by the pressure supplied via the pressure supply opening. However, the sample often contains viruses, bacteria or other contaminants, and the contaminants can travel to the analyzer or the outer environment via the pressure supply opening. Such contaminants not only cause inaccurate test results, but also endanger the health of the operator.

BRIEF SUMMARY OF THE INVENTION

In one embodiment, an extraction cassette is provided. The extraction cassette includes an extraction module and a liquid receiving module. The liquid receiving module communicates with the extraction module. The liquid receiving module includes a receiving module body, a sample compartment, a sealing member, an alcohol compartment and a first path. The receiving module body includes a first side, a second side and a sample feeding hole, wherein the first side is opposite the second side, and the sample feeding hole is formed on the first side. The sample compartment is formed on the receiving module body, wherein the sample compartment communicates with the sample feeding hole, the sample compartment includes a first sample compartment connection hole and a second sample compartment connection hole, and the first sample compartment connection hole nears the first side relative to the second side. The sealing member is adapted to seal the sample feeding hole. The alcohol compartment is formed on the receiving module body. The alcohol compartment communicates with the first sample compartment connection hole of the first sample compartment via the first path, wherein at least one portion of the first path is located between the alcohol compartment and the second side.

In one embodiment, the alcohol compartment includes an alcohol compartment connection hole, the alcohol compartment connection hole nears the second side relative to the first side, and the first path connects the alcohol compartment connection hole to the first sample compartment connection hole.

In one embodiment, the liquid receiving module further includes a first mixing compartment and a second path, the first mixing compartment is formed on the receiving module body, the second sample compartment connection hole nears the second side relative to the first side, and the second path connects the second sample compartment connection hole to the first mixing compartment.

In one embodiment, the liquid receiving module further includes a second mixing compartment, a third path and a fourth path, the second mixing compartment is formed on the receiving module body, the third path connects the first mixing compartment to the second mixing compartment, the fourth path connects the second mixing compartment to the extraction module, the fourth path includes a fourth path outlet, the fourth path outlet nears the second side relative to the first mixing compartment and the second mixing compartment.

In one embodiment, the liquid receiving module further includes a first detergent compartment, a second detergent compartment, a fifth path and a sixth path, the first detergent compartment and the second detergent compartment are formed on the receiving module body, the fifth path connects the first detergent compartment to the first mixing compartment, and the sixth path connects the second detergent compartment to the first mixing compartment.

In one embodiment, the liquid receiving module further includes an eluent compartment and a seventh path, the eluent compartment is formed on the receiving module body, and the seventh path connects the eluent compartment to the extraction module.

In one embodiment, a method for extracting nucleic acid is provided. The method for extracting nucleic acid includes the following steps. First, an extraction cassette is provided, wherein the extraction cassette includes a liquid receiving module and an extraction module, the extraction module communicates with the liquid receiving module, the liquid receiving module includes a sample compartment, an alcohol compartment, a first mixing compartment, a second mixing compartment, a first detergent compartment, a second detergent compartment and a eluent compartment. Then, an alcohol is filled into the alcohol compartment, a first detergent is filled into the first detergent compartment, a second detergent is filled into the second detergent compartment, and an eluent is filled into the eluent compartment. Next, a sample is filled into the sample compartment. Then, the sample inside the sample compartment is heated.

In one embodiment, the method further includes moving the alcohol from the alcohol compartment to the sample compartment, wherein the sample and the alcohol are mixed into a mixed liquid.

In one embodiment, the method further includes the following steps. First, the mixed liquid is moved into the first mixing compartment. Then, the mixed liquid is moved between the first mixing compartment and the second mixing compartment repeatedly to mix the sample and the alcohol.

In one embodiment, the method further includes the following steps. First, the mixed liquid is moved into the extraction module and the nucleic acid is captured from the mixed liquid by the extraction module. Then, the mixed liquid is moved into a first waste-liquid compartment of the extraction module.

In one embodiment, the method further includes the following steps. First, the first detergent is progressively moved from the first detergent compartment to the first mixing compartment and the second mixing compartment to clean the first mixing compartment and the second mixing compartment. Then, the first detergent is moved to the extraction module to clean the extraction module. Next, the first detergent is moved to the first waste-liquid compartment of the extraction module.

In one embodiment, the method further includes the following steps. First, the second detergent is progressively moved from the second detergent compartment to the first mixing compartment and the second mixing compartment to clean the first mixing compartment and the second mixing compartment. Then, the second detergent is moved to the extraction module to clean the extraction module. Next, at least one portion of the second detergent is moved to a second waste-liquid compartment of the extraction module.

In one embodiment, the method further includes moving the eluent from the eluent compartment to the extraction module to take out the nucleic acid from the extraction module.

Utilizing the extraction cassette of the embodiment of the present invention, the sample feeding hole of the sample compartment is sealed by the sealing member. The mixed liquid inside the sample compartment is moved to the first mixing compartment by the pressure applied to the alcohol compartment. Therefore, the virus, bacteria and other contaminants of the sample in the sample compartment is prevented from leaking from the liquid receiving module. Even if the contaminants of the sample enter the alcohol compartment via the first sample compartment connection hole (above the sample compartment) and the first path, the contaminants are disinfected by the alcohol compartment and are unable to cause pollution. The extraction cassette of the embodiment of the present invention can restrict the area polluted by the sample to the environment inside or around the analyzer, improving the accuracy of the analysis result and safeguarding the health of the operator.

A detailed description is given in the following embodiments with reference to the accompanying drawings.

BRIEF DESCRIPTION OF THE DRAWINGS

The present invention can be more fully understood by reading the subsequent detailed description and examples with references made to the accompanying drawings, wherein.

DETAILED DESCRIPTION OF THE INVENTION

The following description is of the best-contemplated mode of carrying out the present invention. This description is made for the purpose of illustrating the general principles of the present invention and should not be taken in a limiting sense. The scope of the present invention is best determined by reference to the appended claims.

Figure 1A:
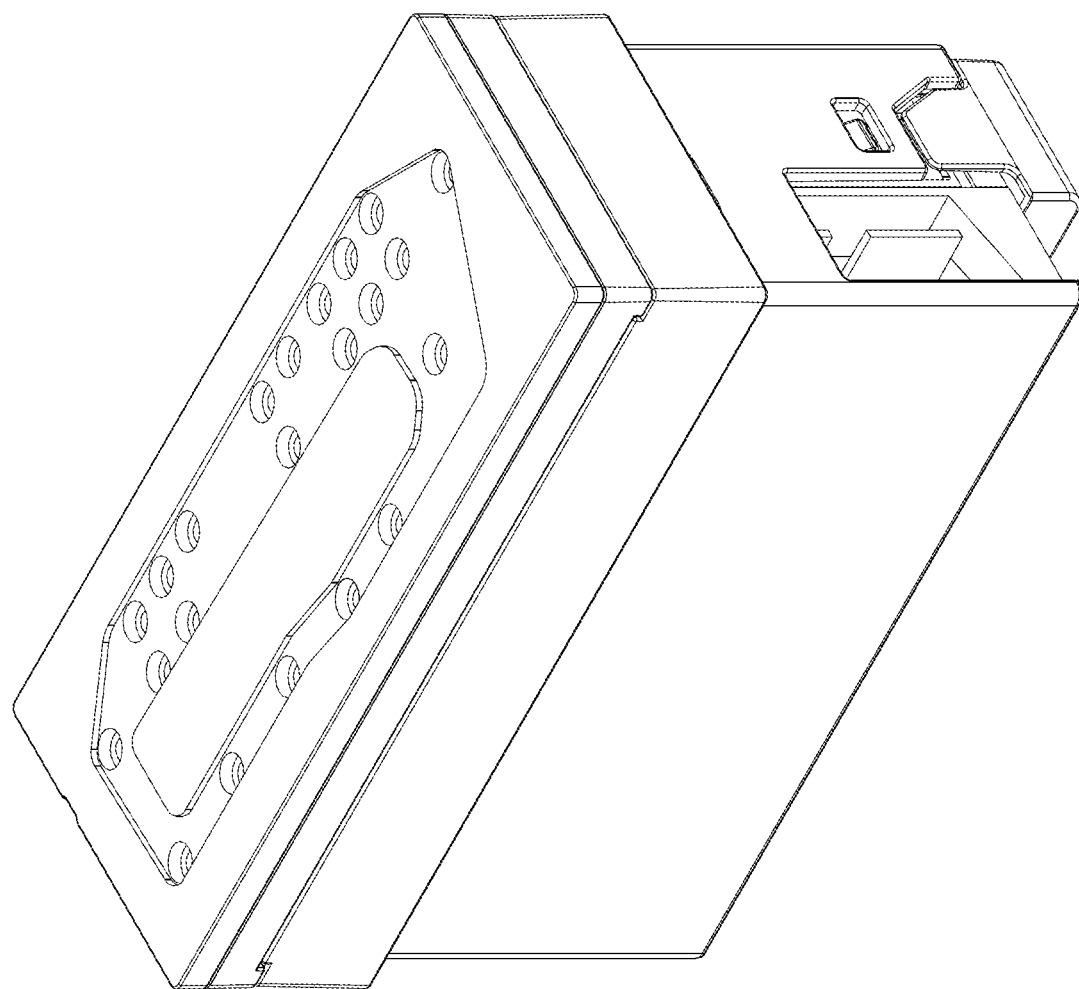
FIG. 1A is an assembled view of an extraction cassette of an embodiment of the present invention.
Figure 1B:
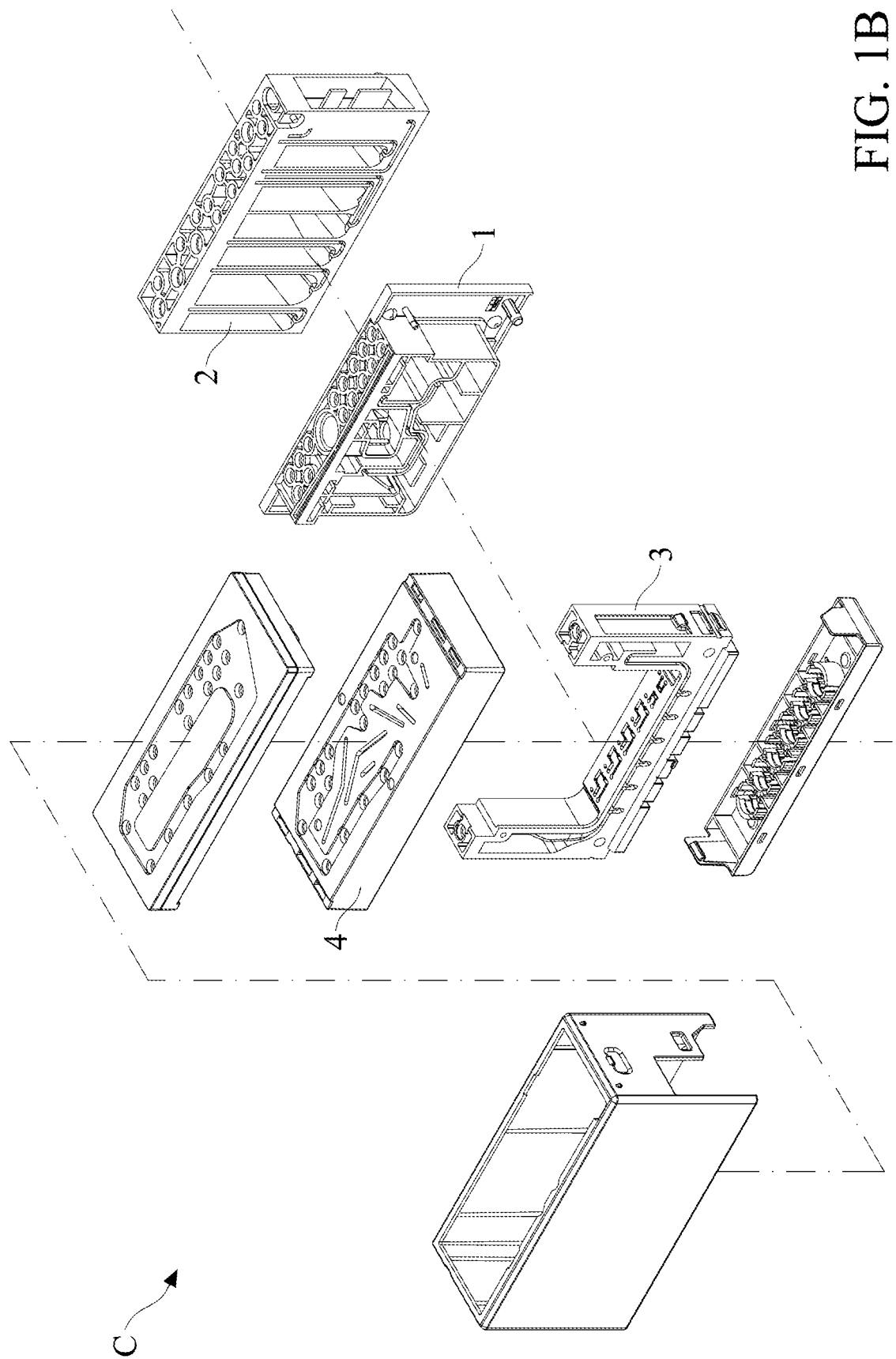
FIG. 1B is an exploded view of the extraction cassette of the embodiment of the present invention.

FIG. 1A is an assembled view of an extraction cassette C of an embodiment of the present invention. FIG. 1B is an exploded view of the extraction cassette C of the embodiment of the present invention. With reference to FIGS. 1A and 1B, the extraction cassette C includes an extraction module 1, a liquid receiving module 2, a sampling module 3 and a connection module 4. The extraction cassette C is adapted to be disposed into an analyzer. The analyzer includes a first pressure supplying module, an analyzing module and a second pressure supplying module. The first pressure supplying module and the second pressure supplying module provide pressure toward the extraction cassette C to control the liquid movement inside the extraction cassette C. The analyzing module heats and cools the extraction cassette C, and analyzes the sample inside extraction cassette C.

Figure 2A:
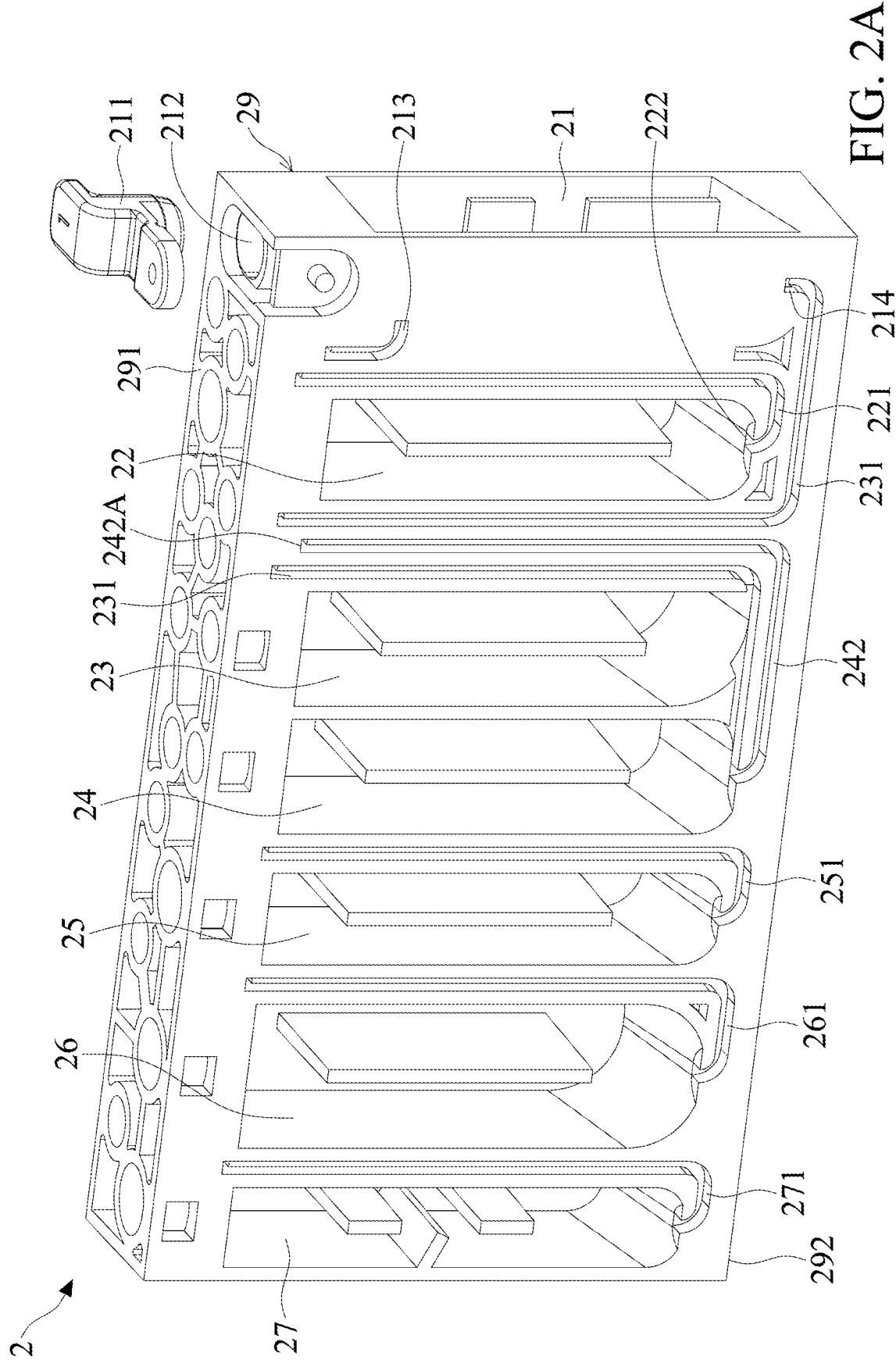
FIG. 2A is a detail of the liquid receiving module of the embodiment of the present invention.

With reference to FIG. 1B, the liquid receiving module 2 communicates with the extraction module 1 via the connection module 4. The compartments of the liquid receiving module 2 communicate with one another via the connection module 4. FIG. 2A is a detail of the liquid receiving module 2. With reference to FIG. 2A, the liquid receiving module 2 includes a receiving module body 29, a sample compartment 21, a sealing member 211, an alcohol compartment 22 and a first path 221. The receiving module body 29 includes a first side 291, a second side 292 and a sample feeding hole 212. The first side 291 is opposite the second side 292. The sample feeding hole 212 is formed on the first side 291. The sample compartment 21 is formed on the receiving module body 29. The sample compartment 21 communicates with the sample feeding hole 212. The sample compartment 21 includes a first sample compartment connection hole 213 and a second sample compartment connection hole 214. The first sample compartment connection hole 213 nears the first side 291 relative to the second side 292. The sealing member 211 is adapted to seal the sample feeding hole 212. The alcohol compartment 22 is formed on the receiving module body 29. The alcohol compartment 22 communicates with the first sample compartment connection hole 213 of the first sample compartment 21 via the first path 221. In one embodiment, wherein at least one portion of the first path 221 is located between the alcohol compartment 22 and the second side 292.

With reference to FIG. 2A, in one embodiment, the alcohol compartment 22 includes an alcohol compartment connection hole 222. The alcohol compartment connection hole 222 nears the second side 292 relative to the first side 291. The first path 221 connects the alcohol compartment connection hole 222 to the first sample compartment connection hole 213.

With reference to FIG. 2A, in one embodiment, the liquid receiving module 2 further includes a first mixing compartment 23 and a second path 231. The first mixing compartment 23 is formed on the receiving module body 29. The second sample compartment connection hole 214 nears the second side 292 relative to the first side 291. The second path 231 connects the second sample compartment connection hole 214 to the first mixing compartment 23.

Figure 2B:
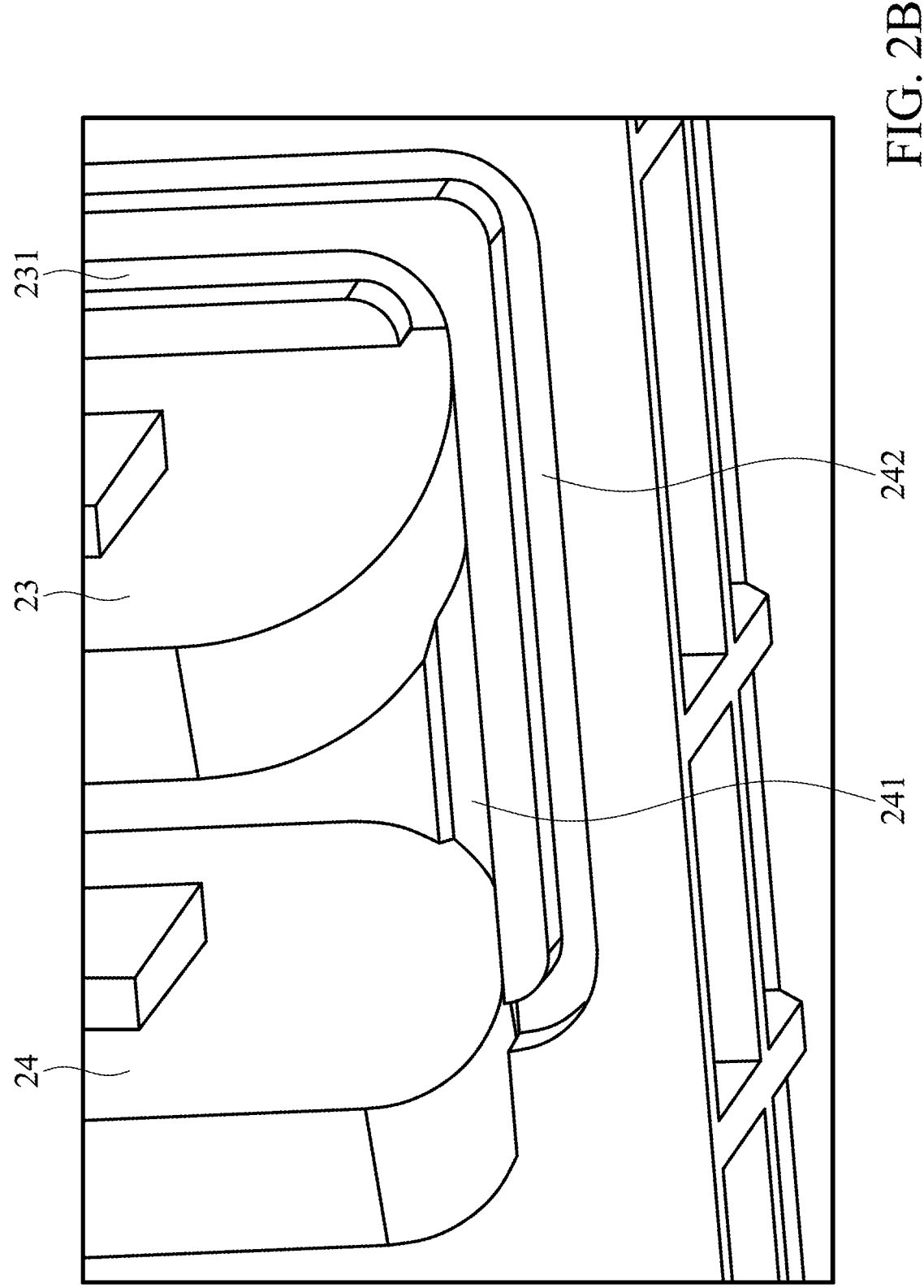
FIG. 2B is a detail of the third path of the embodiment of the present invention.

With reference to FIGS. 2A and 2B, in one embodiment, the liquid receiving module 2 further includes a second mixing compartment 24, a third path 241 and a fourth path 242. The second mixing compartment 24 is formed on the receiving module body 29. The third path 241 connects the first mixing compartment 23 to the second mixing compartment 24. The fourth path 242 connects the second mixing compartment 24 to the extraction module 1. In one embodiment, the third path 241 connects the first mixing compartment 23 to the bottom of the second mixing compartment 24.

With reference to FIG. 2A, in one embodiment, the liquid receiving module 2 further includes a first detergent compartment 25, a second detergent compartment 26, a fifth path 251 and a sixth path 261. The first detergent compartment 25 and the second detergent compartment 26 are formed on the receiving module body 29. The fifth path 251 connects the first detergent compartment 25 to the first mixing compartment 23. The sixth path 261 connects the second detergent compartment 26 to the first mixing compartment 23.

With reference to FIG. 2A, in one embodiment, the liquid receiving module further includes an eluent compartment 27 and a seventh path 271. The eluent compartment 27 is formed on the receiving module body 29, and the seventh path 271 connects the eluent compartment 27 to the extraction module 1.

Figure 3A:
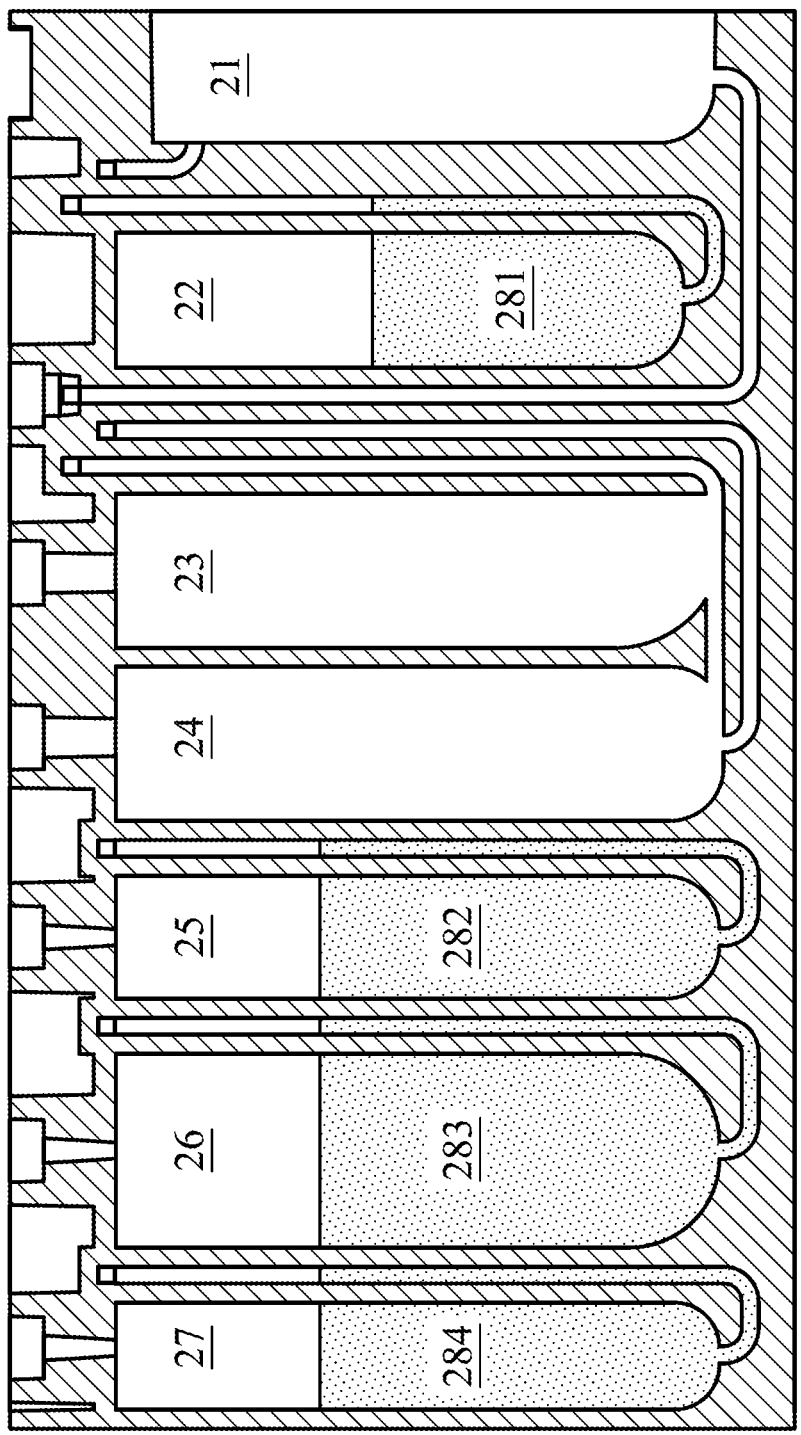
FIGS. 3A, 3B, 3C, 3D, 3E, 3F, 3G, 3H and 3I show the operation of the liquid receiving module of the embodiment of the present invention.
Figure 3B:
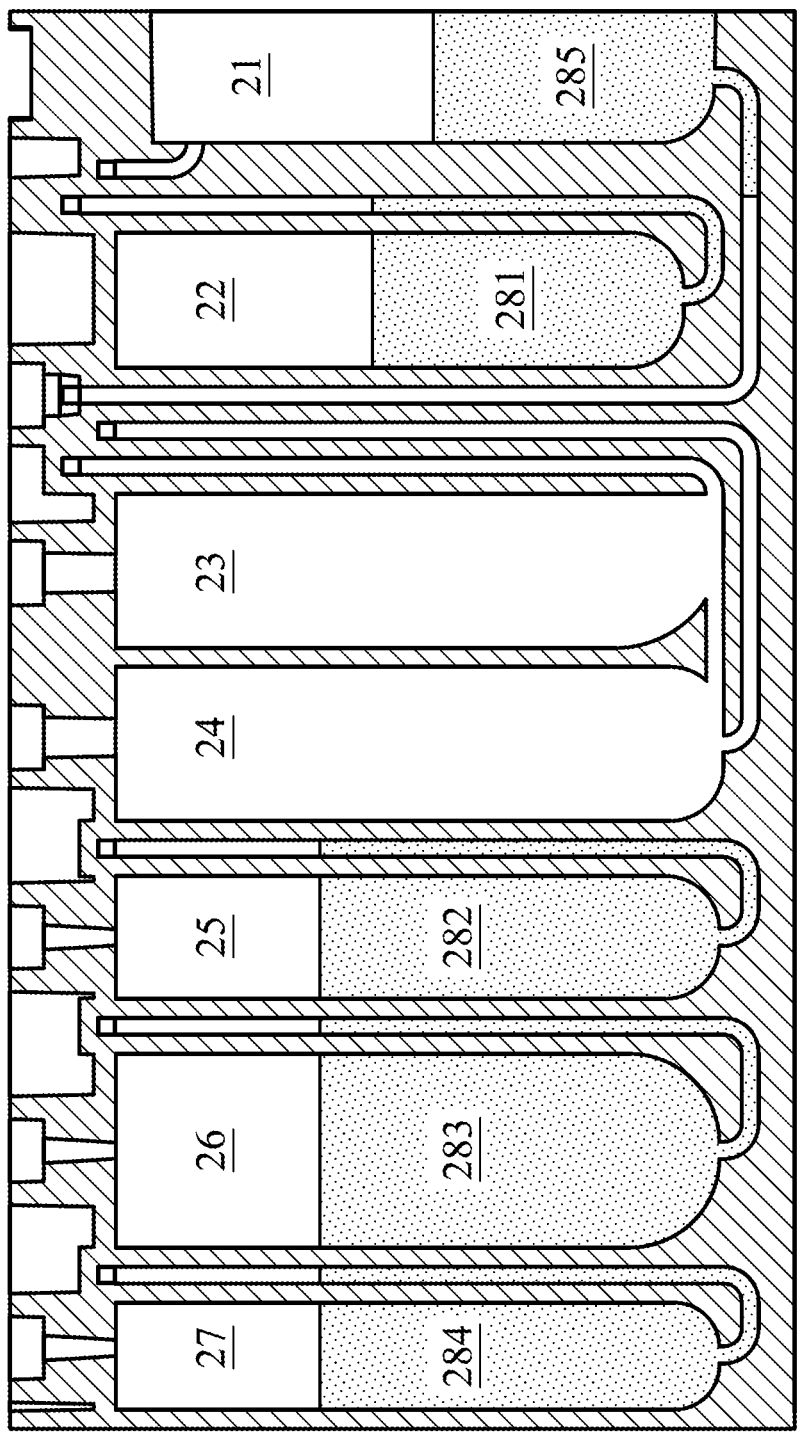
Figure 3C:
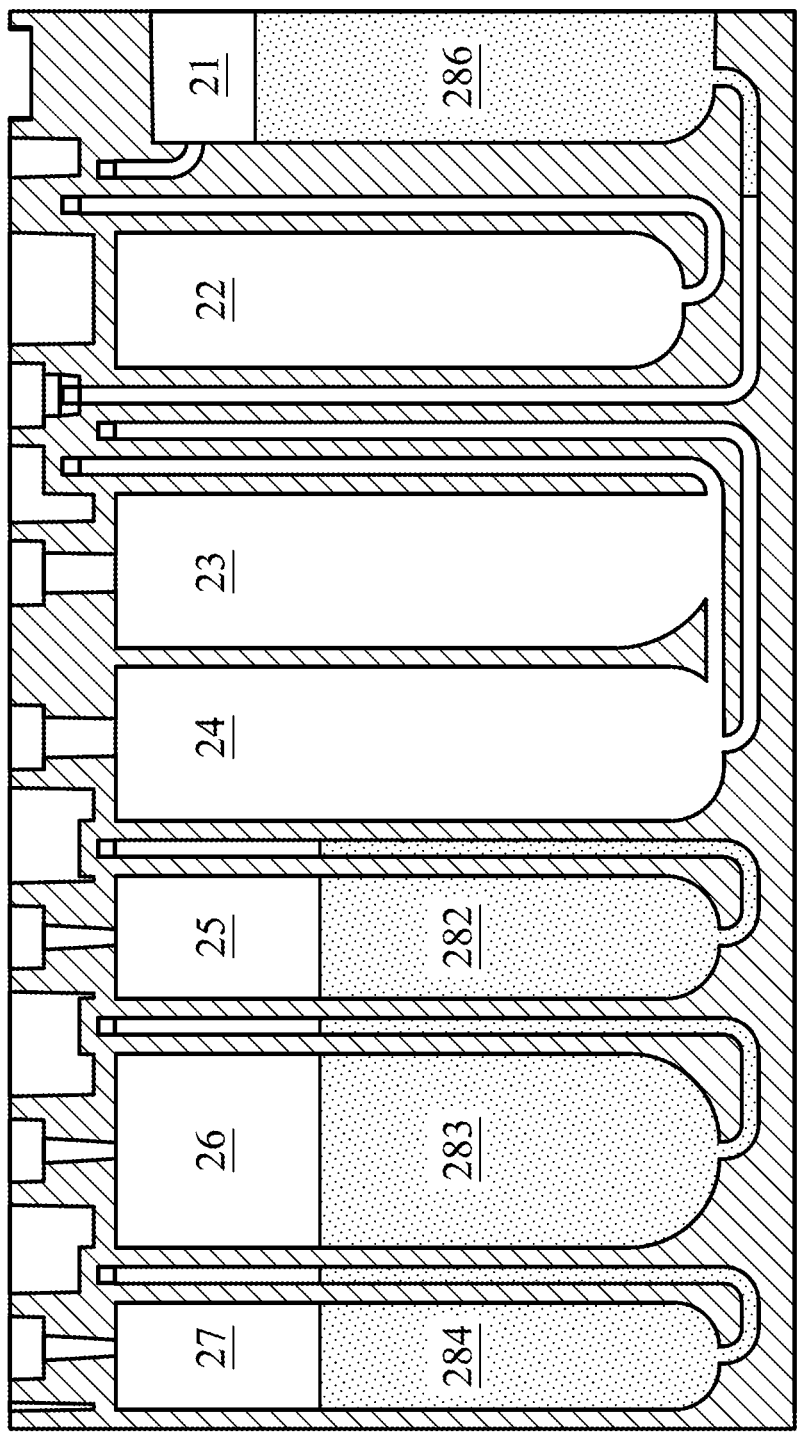
Figure 3D:
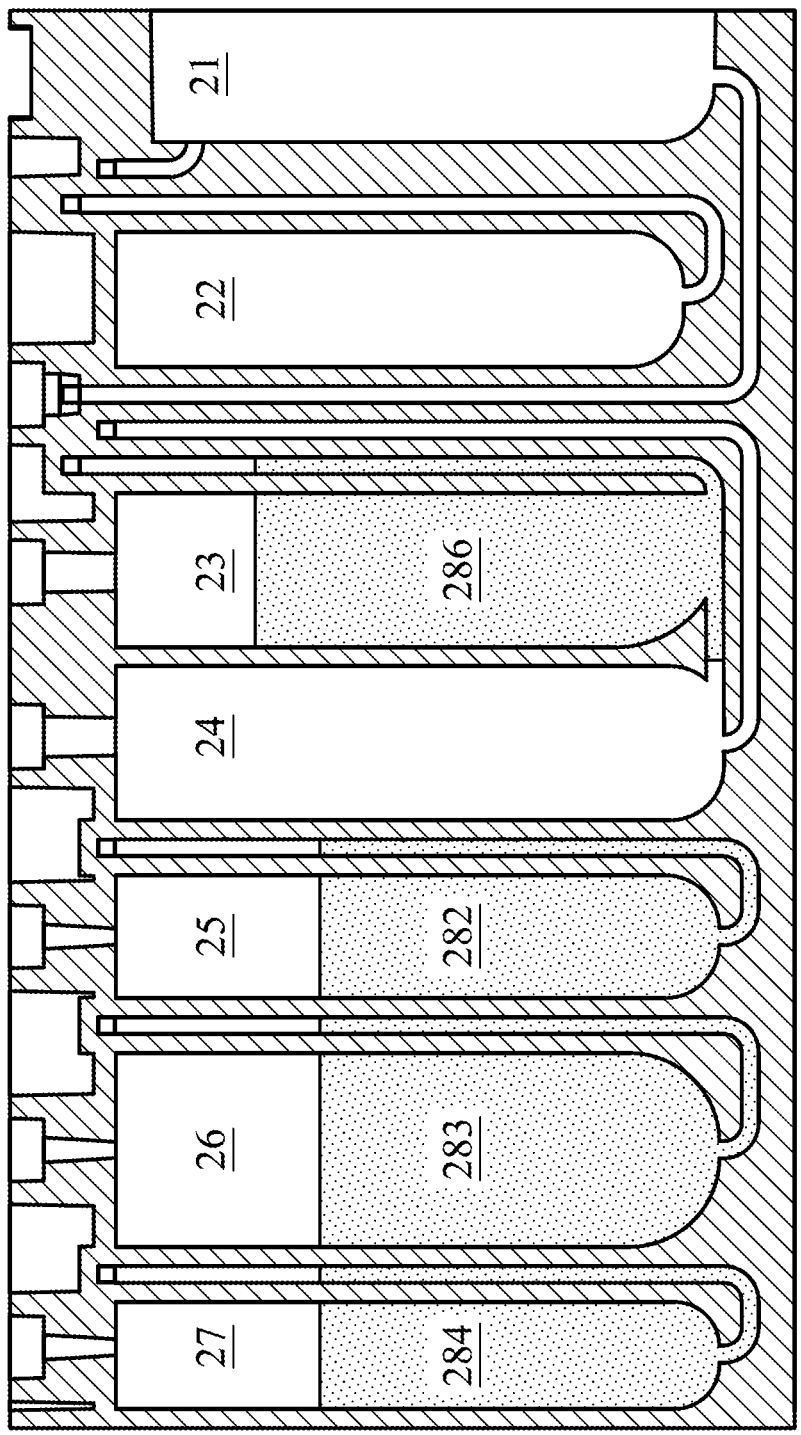
Figure 3E:
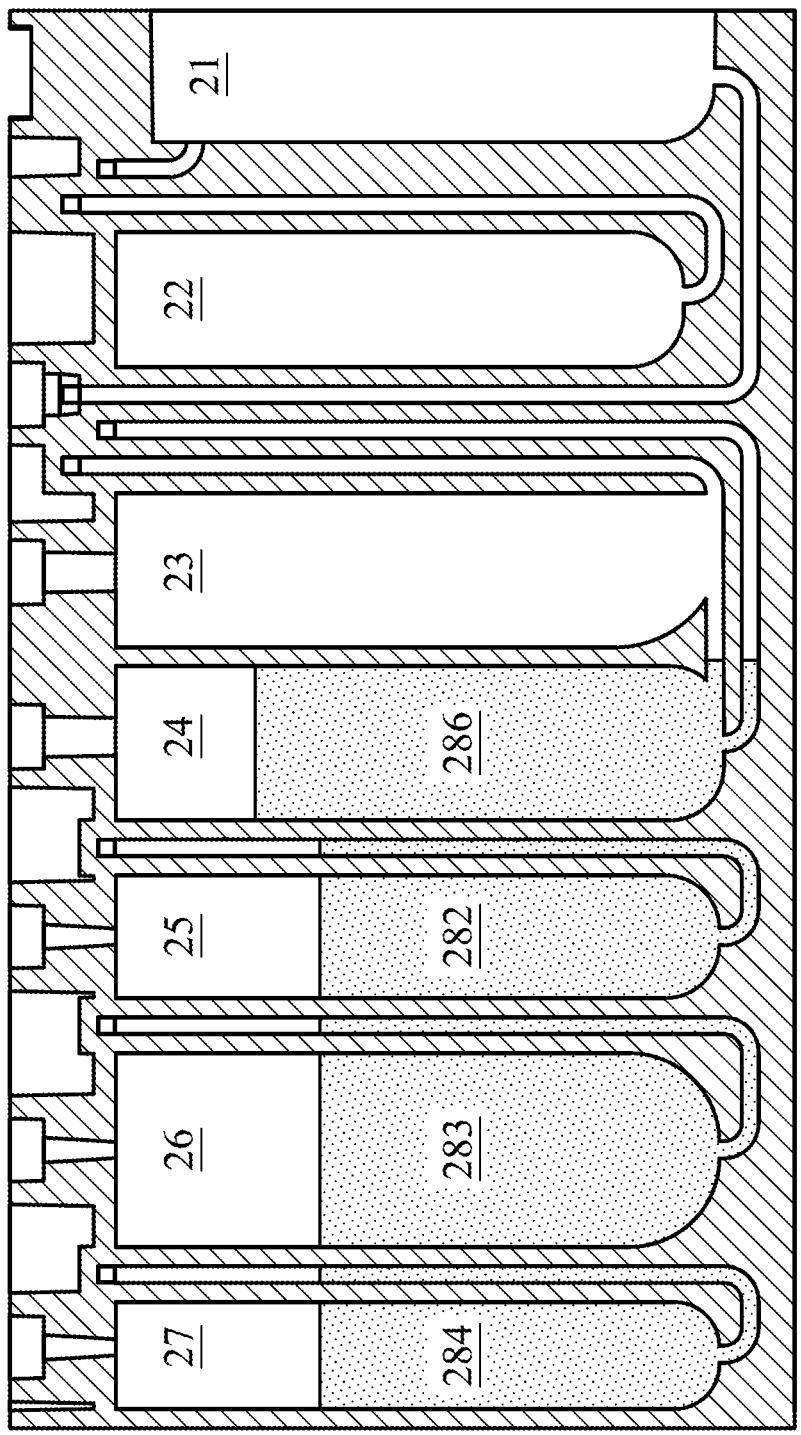

FIGS. 3A-3I show the operation of the liquid receiving module 2 of the embodiment of the present invention. With reference to FIG. 3A, first, liquid receiving module 2 receives four liquids, which are the alcohol 281 (in the alcohol compartment 22), the first detergent 282 (in the first detergent compartment 25), the second detergent 283 (in the second detergent compartment 26) and the eluent 284 (in the eluent compartment 27). Next, with reference to FIG. 3B, the sample 285 is filled into the sample compartment 21. After the extraction cassette C is disposed into the analyzing module of the analyzer, the temperature of the sample 285 in the sample compartment 21 is raised to 60 degrees Celsius (60° C.). Then, with reference to FIG. 3C, after the temperature of the sample 285 in the sample compartment 21 is raised to 60 degrees Celsius (60° C.), the alcohol 281 from the alcohol compartment 22 to the sample compartment 21, wherein the sample 285 and the alcohol 281 are mixed into a mixed liquid 286 in the sample compartment 21. Next, with reference to FIGS. 3D and 3E, the mixed liquid 286 with the sample 285 and the alcohol 281 is moved from the sample compartment 21 to the first mixing compartment 23 (FIG. 3D). Then, the mixed liquid 286 is moved between the first mixing compartment 23 and the second mixing compartment 24 repeatedly to mix the sample 285 and the alcohol 281 (FIG. 3E).

In one embodiment, the mixed liquid 286 with the sample 285 and the alcohol 281 is moved into the extraction module 1 and the nucleic acid is captured from the mixed liquid 286 by the extraction module 1. Then, the mixed liquid 286 is moved into a first waste-liquid compartment of the extraction module 1.

Figure 3F:
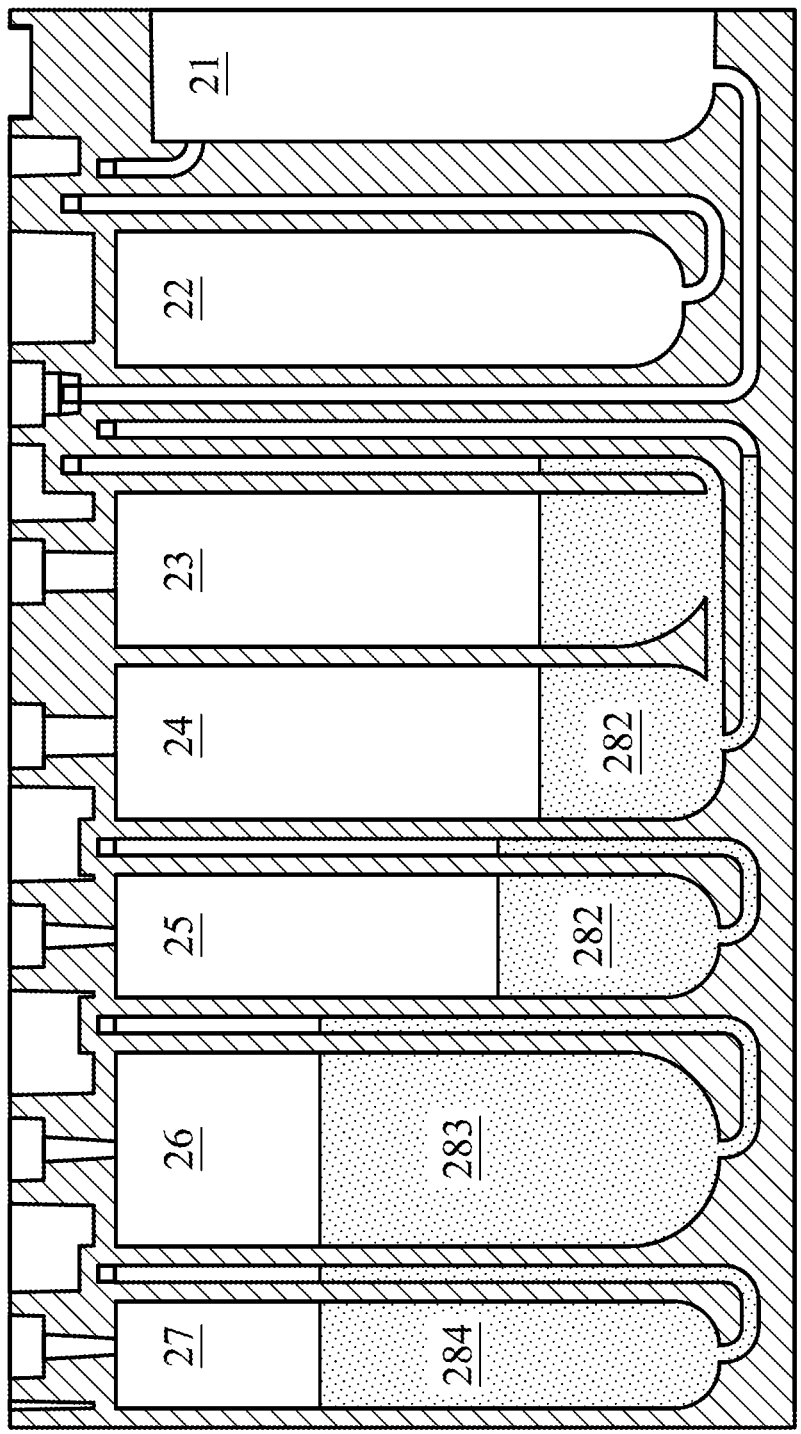
Figure 3G:
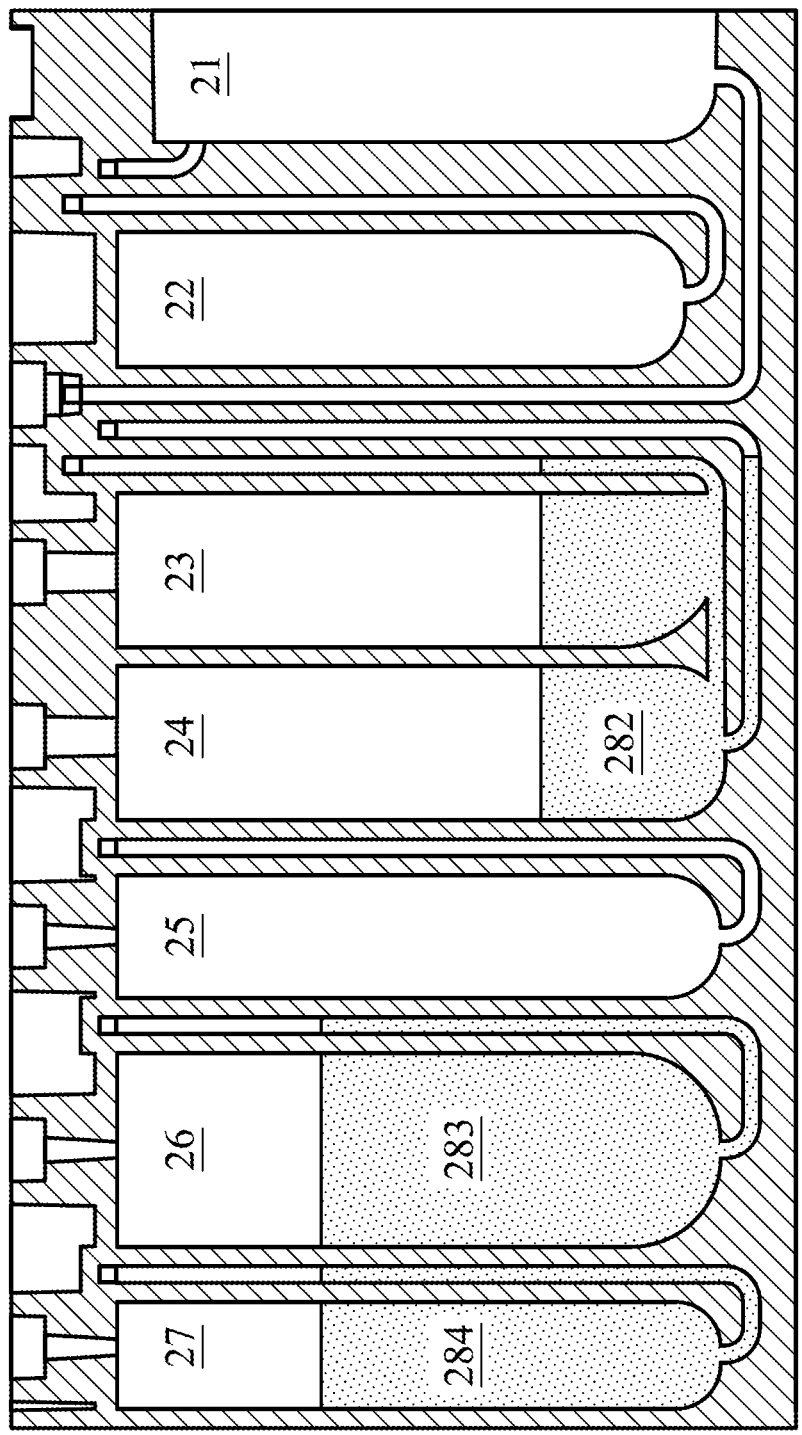

With reference to FIGS. 3F and 3G, next, the first detergent 282 is progressively moved from the first detergent compartment 25 to the first mixing compartment 23 and the second mixing compartment 24 to clean the first mixing compartment 23 and the second mixing compartment 24. Then, the first detergent 282 is moved to the extraction module 1 to clean the extraction module 1. Next, the first detergent 282 is moved to the first waste-liquid compartment of the extraction module 1.

Figure 3H:
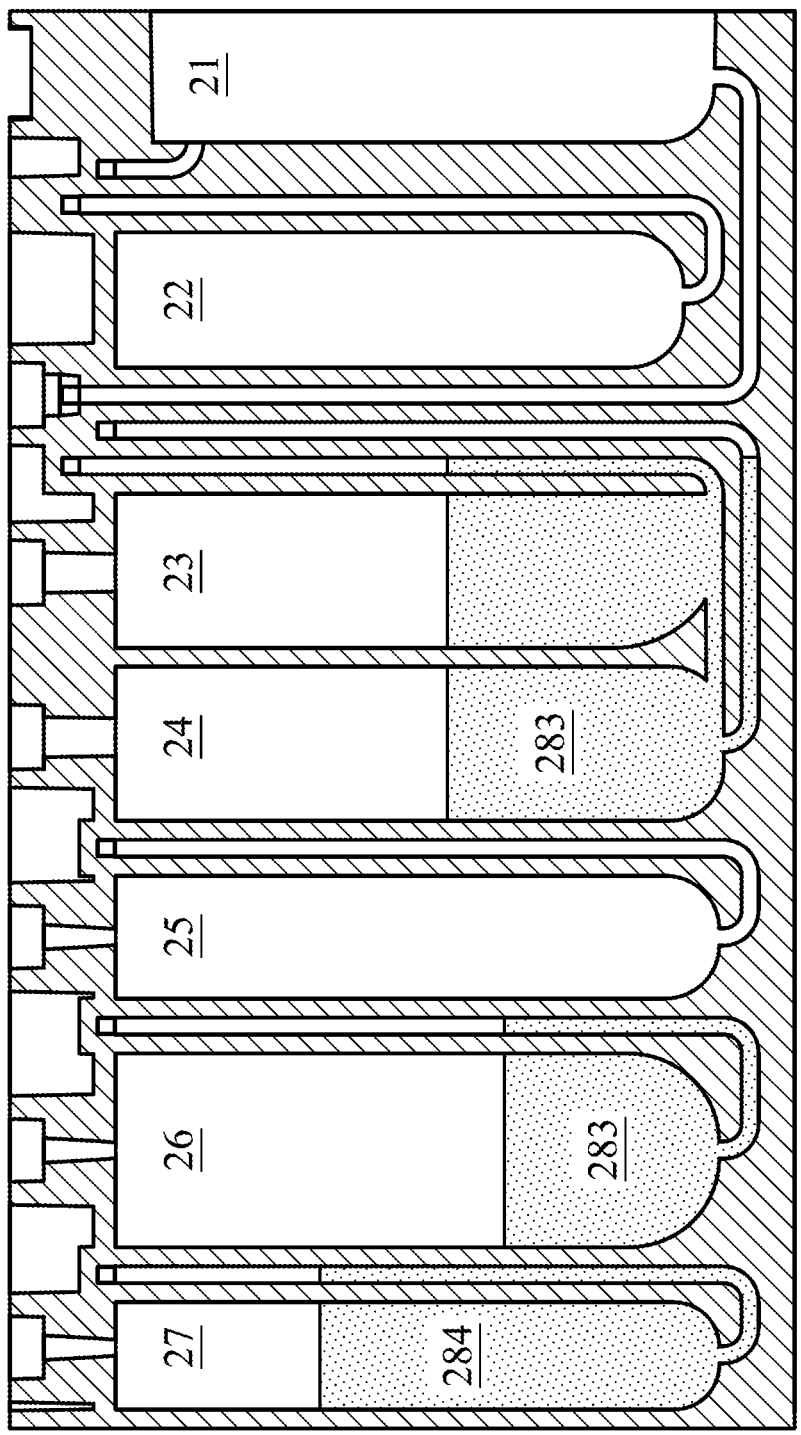
Figure 3I:
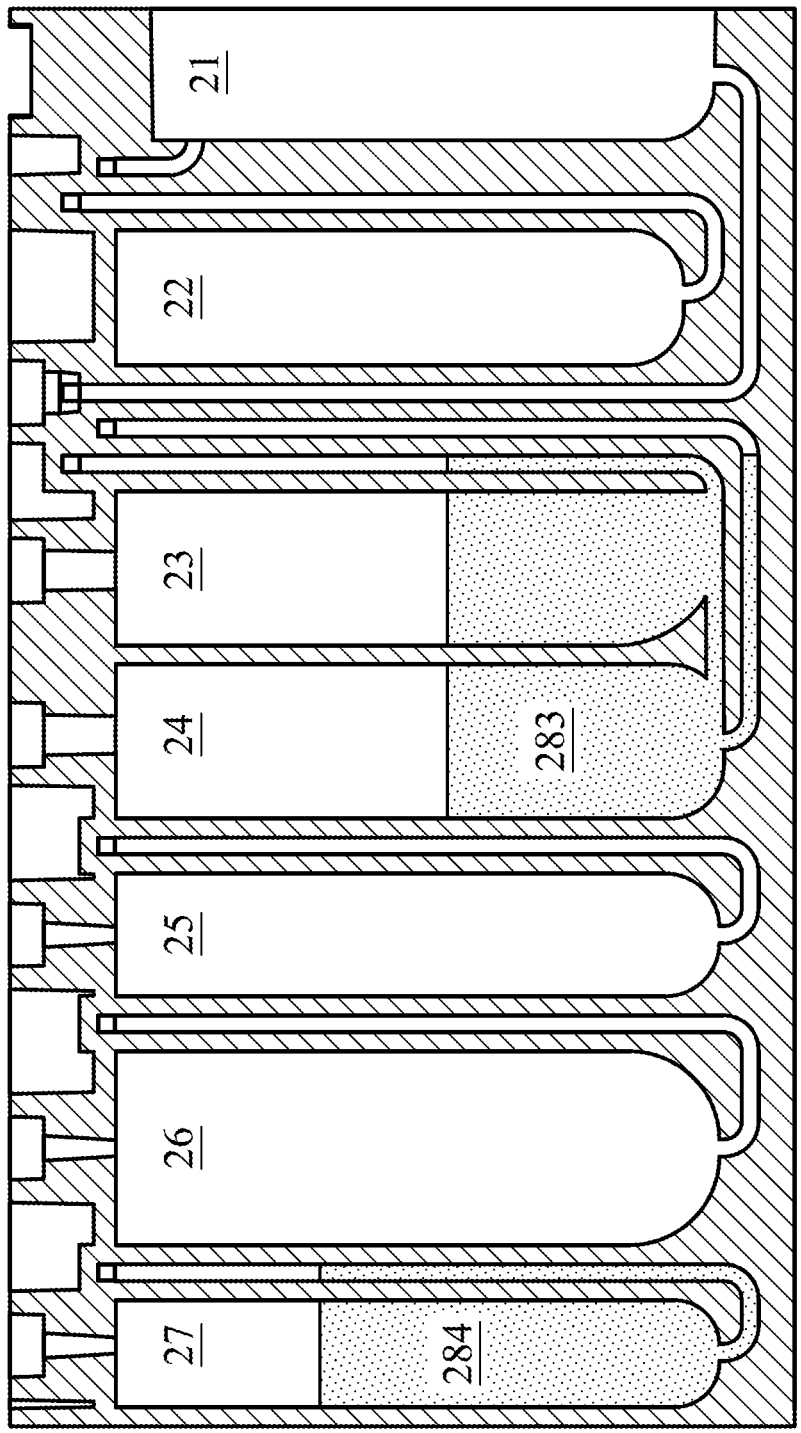

Then, with reference to FIGS. 3H and 3I, the second detergent 283 is progressively moved from the second detergent compartment 26 to the first mixing compartment 23 and the second mixing compartment 24 to clean the first mixing compartment 23 and the second mixing compartment 24. Then, the second detergent 283 is moved to the extraction module 1 to clean the extraction module 1. Next, at least one portion of the second detergent 283 is moved to a second waste-liquid compartment of the extraction module 1.

Finally, the eluent 284 is from the eluent compartment 27 to the extraction module 1 to take out the nucleic acid from the extraction module 1. The eluent 284 with the nucleic acid is then moved to the sampling module 3 to be quantitatively sampled.

Utilizing the extraction cassette of the embodiment of the present invention, with reference to FIGS. 2A and 3B, the sample feeding hole 212 of the sample compartment 21 is sealed by the sealing member 211. The mixed liquid 286 inside the sample compartment 21 is moved to the first mixing compartment 23 by the pressure applied to the alcohol compartment 22. Therefore, the virus, bacteria and other contaminants of the sample 285 in the sample compartment 21 is prevented from leaking from the liquid receiving module. Even if the contaminants of the sample 285 enter the alcohol compartment 22 via the first sample compartment connection hole (above the sample compartment 21) and the first path 221, the contaminants are disinfected by the alcohol compartment 22 and are unable to cause pollution. The extraction cassette of the embodiment of the present invention can restrict the area polluted by the sample 285 to the environment inside or around the analyzer, improving the accuracy of the analysis result and safeguarding the health of the operator.

With reference to FIGS. 2A, 3D and 3E, utilizing the extraction cassettes of the embodiment of the present invention, the mixed liquid 286 can be moved back and forth between the first mixing chamber 23 and the second mixing chamber 24 via the third path 241. The mixed liquid 286 is thoroughly mixed, whereby the effect of sufficiently mixing the mixed liquid 286 can be achieved with a minimum space. In one embodiment, the fourth path 242 has a fourth path outlet 242A that is higher than the top of the first mixing chamber 23 and the second mixing chamber 24. The fourth path outlet 242A is higher than the liquid level of the mixed liquid 286. Thus the mixed liquid 286 is prevented from entering the extraction module 1 unintentionally through the fourth path outlet 242A.

With reference to FIG. 2A, the liquid receiving module 2 can be integrally formed except the sealing member 211.

Figure 4A:
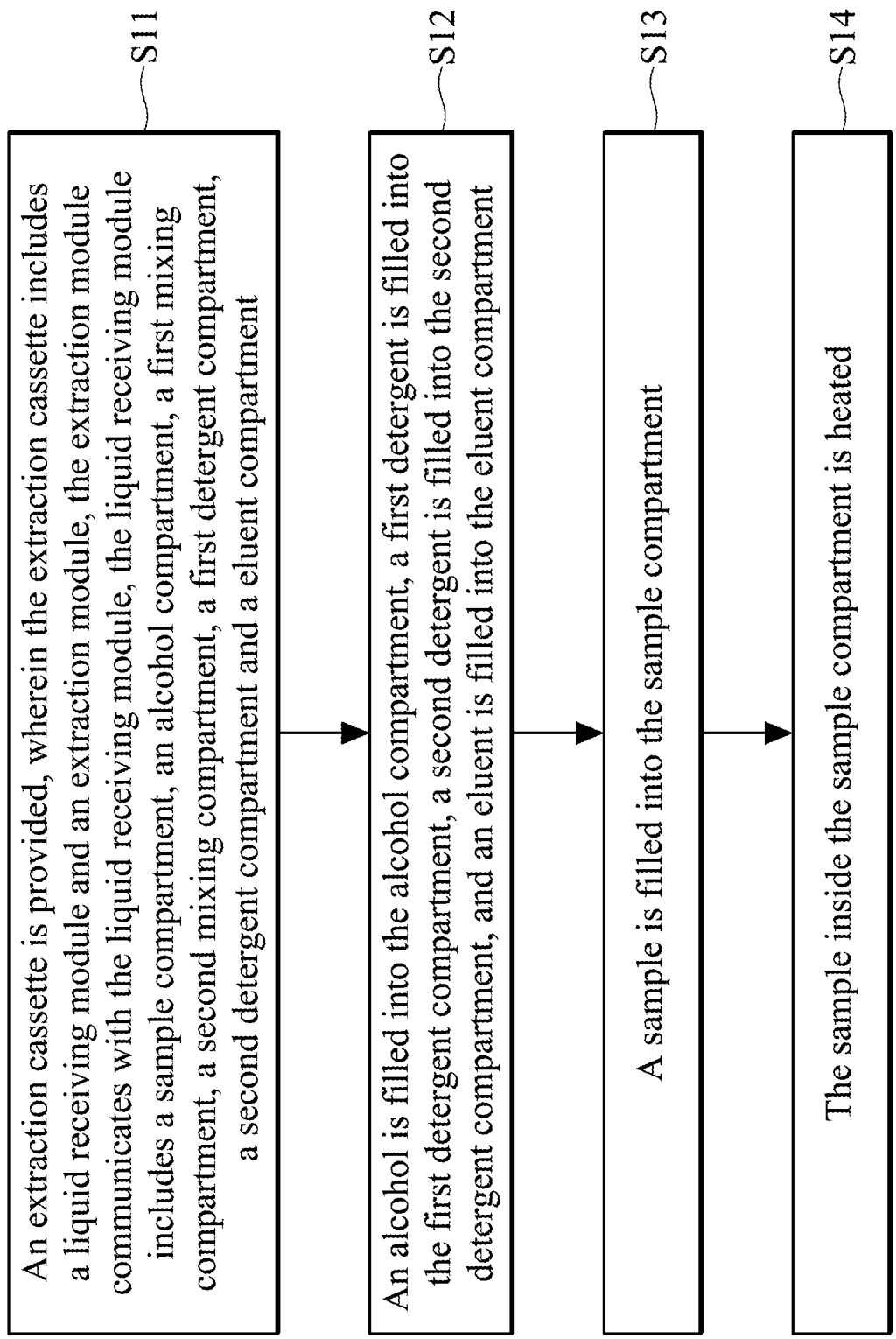
FIGS. 4A, 4B and 4C show a method for extracting nucleic acid of the embodiment of the present invention.
Figure 4B:
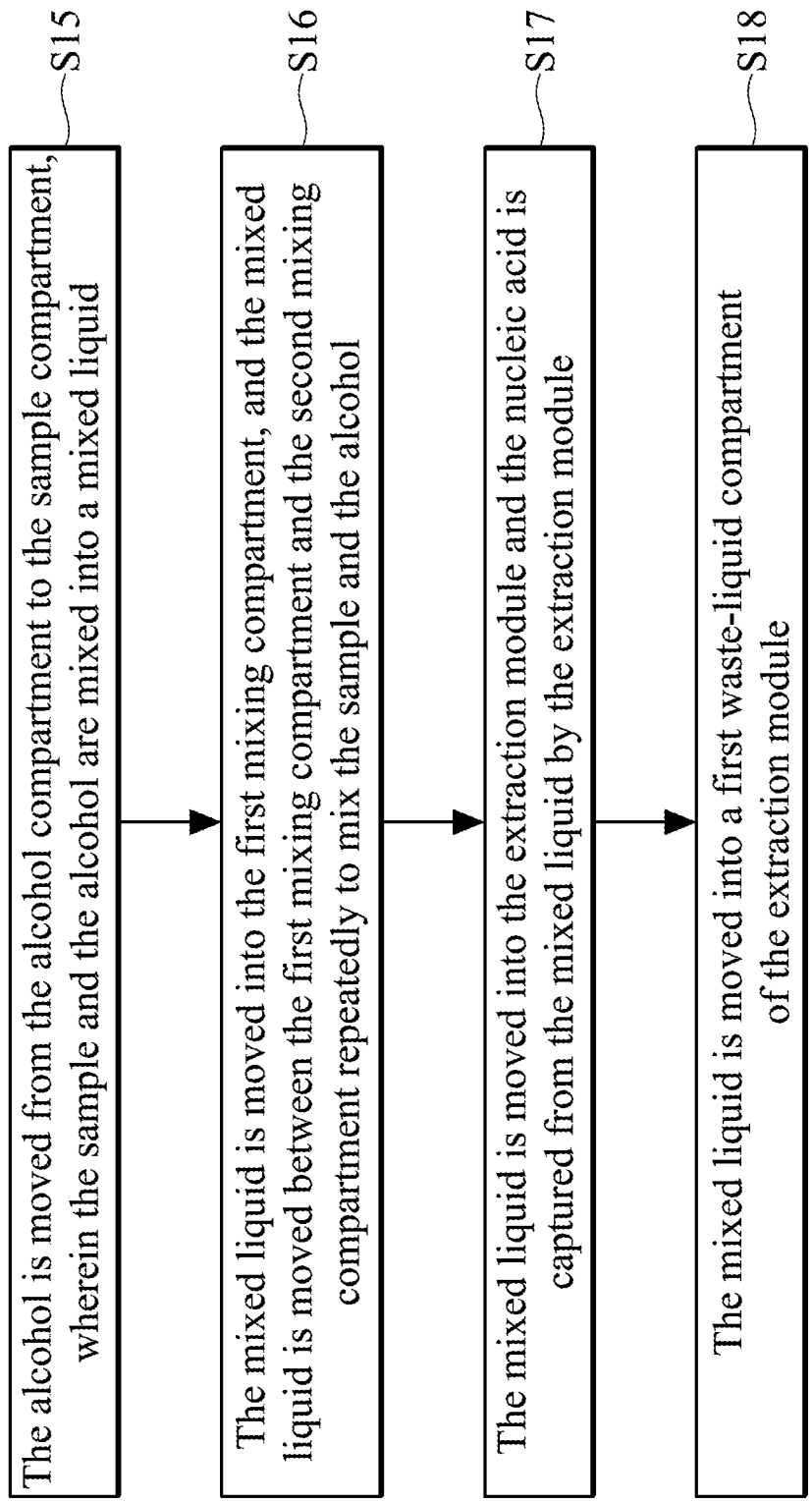
Figure 4C:
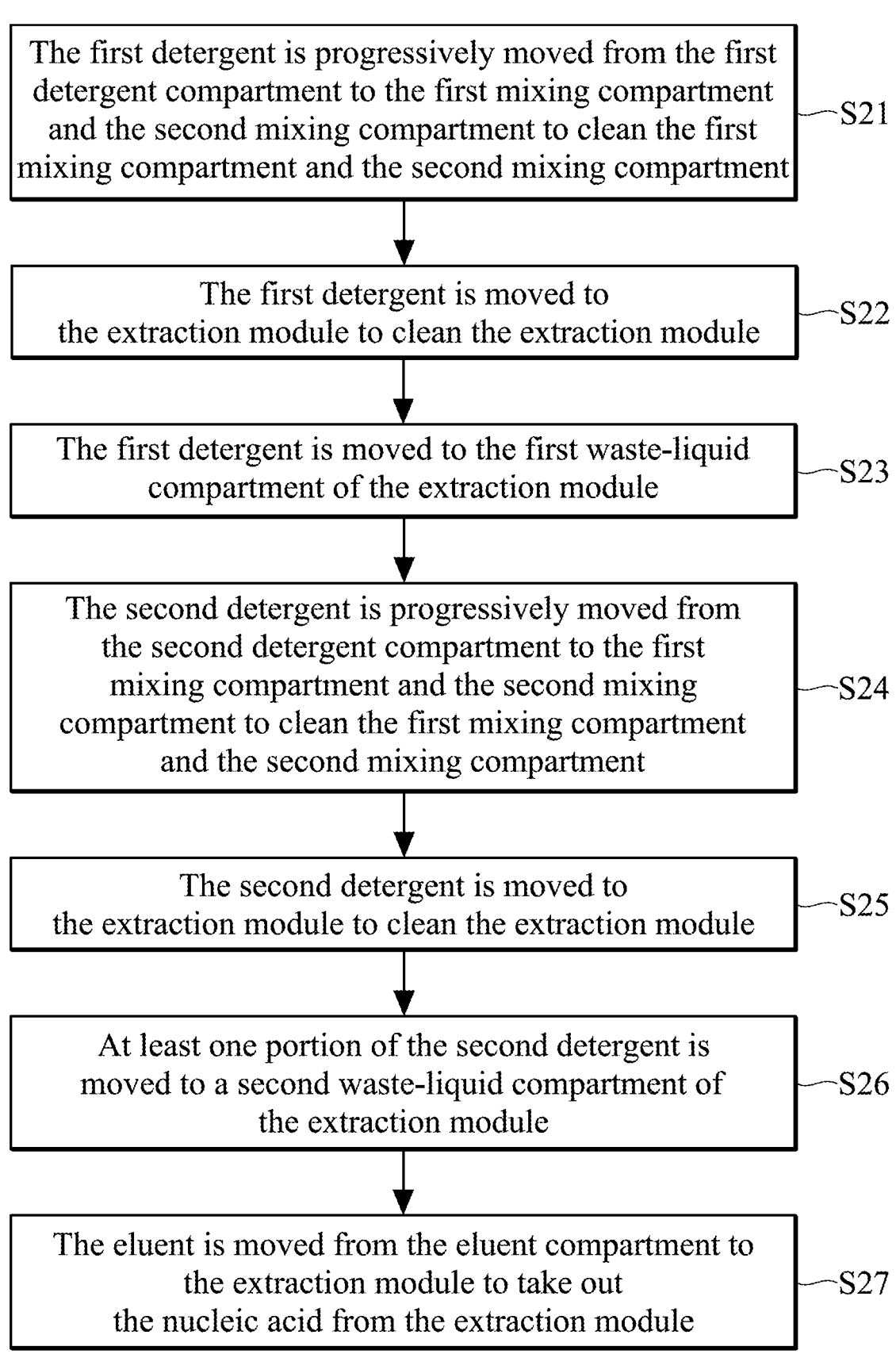

FIGS. 4A-4C show a method for extracting nucleic acid of an embodiment of the present invention. With reference to FIG. 4A, the method for extracting nucleic acid of the embodiment of the present invention includes the following steps. First, an extraction cassette is provided, wherein the extraction cassette includes a liquid receiving module and an extraction module, the extraction module communicates with the liquid receiving module, the liquid receiving module includes a sample compartment, an alcohol compartment, a first mixing compartment, a second mixing compartment, a first detergent compartment, a second detergent compartment and a eluent compartment (S11). Then, an alcohol is filled into the alcohol compartment, a first detergent is filled into the first detergent compartment, a second detergent is filled into the second detergent compartment, and an eluent is filled into the eluent compartment (S12). Next, a sample is filled into the sample compartment (S13). Then, the sample inside the sample compartment is heated (S14).

With reference to FIG. 4B, in one embodiment, the method further includes the following steps. The alcohol is moved from the alcohol compartment to the sample compartment, wherein the sample and the alcohol are mixed into a mixed liquid (S15). Next, the mixed liquid is moved into the first mixing compartment, and then the mixed liquid is moved between the first mixing compartment and the second mixing compartment repeatedly to mix the sample and the alcohol (S16). Next, the mixed liquid is moved into the extraction module and the nucleic acid is captured from the mixed liquid by the extraction module (S17). Then, the mixed liquid is moved into a first waste-liquid compartment of the extraction module (S18).

With reference to FIG. 4C, in one embodiment, the method further includes the following steps. The first detergent is progressively moved from the first detergent compartment to the first mixing compartment and the second mixing compartment to clean the first mixing compartment and the second mixing compartment (S21). Then, the first detergent is moved to the extraction module to clean the extraction module (S22). Next, the first detergent is moved to the first waste-liquid compartment of the extraction module (S23). Then, the second detergent is progressively moved from the second detergent compartment to the first mixing compartment and the second mixing compartment to clean the first mixing compartment and the second mixing compartment (S24). Then, the second detergent is moved to the extraction module to clean the extraction module (S25). Next, at least one portion of the second detergent is moved to a second waste-liquid compartment of the extraction module (S26). Then, the eluent is moved from the eluent compartment to the extraction module to take out the nucleic acid from the extraction module (S27).

In one experiment, the applicant used an oral cell preservation solution containing a high concentration of the nucleic acid to be tested (Mh plasmid: 106 copies/mL, CytB plasmid) as a positive sample, and an oral cell preservation solution containing no nucleic acid to be tested as a negative sample, and perform interleaved tests of positive and negative samples. It is desired to confirm that the negative sample test result after the positive sample test result has no nucleic acid detected. It has been experimentally verified that the extraction cassette of the embodiment of the present invention can effectively prevent cross-contamination.

| Test 1: High concentration positive and negative samples are alternatively tested four times (test sequence: positive → negative → positive → negative) Result: no nucleic acid detected in negative samples | | | | |
|---|---|---|---|---|
| Samples | positive | negative | positive | negative |
| Mh plasmid1 Cq | 25.11 | N/A | 26.48 | N/A |
| CytB plasmid Cq | 24.54 | N/A | 28.1 | N/A |

| Test 2: Negative sample test after five high consecution positive sample tests (test sequence: positive → positive → positive → positive → negative) Result: no nucleic acid detected in negative samples | | | | | |
|---|---|---|---|---|---|
| Samples | positive | positive | positive | positive | negative |
| Mh plasmid1 Cq | 28.33 | 27.81 | 27.18 | 24.82 | 26.44 | N/A |
| CytB plasmid Cq | 26.89 | 23.51 | 25.85 | 24.68 | 28.58 | N/A |

Use of ordinal terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having the same name (but for use of the ordinal term).

While the present invention has been described by way of example and in terms of the preferred embodiments, it should be understood that the present invention is not limited to the disclosed embodiments. On the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. An extraction cassette, comprising:
   an extraction module; and
   a liquid receiving module, which communicates with the extraction module, the liquid receiving module comprising:
   a receiving module body, comprising a first side, a second side and a sample feeding hole, wherein the first side is opposite the second side, and the sample feeding hole is formed on the first side;
   an alcohol compartment, formed in the receiving module body, the alcohol compartment containing alcohol;
   a sample compartment, formed in the receiving module body, wherein the sample compartment communicates with the sample feeding hole, the sample compartment comprises a first sample compartment connection hole and a second sample compartment connection hole, and the first sample compartment connection hole nears the first side relative to the second side;
   a sealing member, adapted to seal the sample feeding hole, the sample compartment containing a sample, wherein the sample and the alcohol are mixed into a mixed liquid in the sample compartment;
   and
   a first channel, by which the alcohol compartment communicates with the first sample compartment connection hole of the sample compartment,
   wherein at least one portion of the first channel is located between the alcohol compartment and the second side,
   wherein the sample compartment and the alcohol compartment are two separate compartments connected by the first channel, and
   wherein the mixed liquid and the sample are moved into the extraction module from the sample compartment and the alcohol in the extraction module extracts the nucleic acid.

2. The extraction cassette as claimed in claim 1, wherein the alcohol compartment comprises an alcohol compartment connection hole, the alcohol compartment connection hole nears the second side relative to the first side, and the first channel connects the alcohol compartment connection hole to the first sample compartment connection hole.

3. The extraction cassette as claimed in claim 2, wherein the liquid receiving module further comprises a first mixing compartment and a second channel, the first mixing compartment is formed in the receiving module body, the second sample compartment connection hole nears the second side relative to the first side, and the second channel connects the second sample compartment connection hole to the first mixing compartment.

4. The extraction cassette as claimed in claim 3, wherein the liquid receiving module further comprises a second mixing compartment, a third channel and a fourth channel, the second mixing compartment is formed in the receiving module body, the third channel connects the first mixing compartment to the second mixing compartment, the fourth channel connects the second mixing compartment to the extraction module, the fourth channel comprises a fourth channel outlet, the fourth channel outlet nears the second side relative to the first mixing compartment and the second mixing compartment.

5. The extraction cassette as claimed in claim 4, wherein the liquid receiving module further comprises a first detergent compartment, a second detergent compartment, a fifth channel and a sixth channel, the first detergent compartment and the second detergent compartment are formed in the receiving module body, the fifth channel connects the first detergent compartment to the first mixing compartment, and the sixth channel connects the second detergent compartment to the first mixing compartment.

6. The extraction cassette as claimed in claim 5, wherein the liquid receiving module further comprises an eluent compartment and a seventh channel, the eluent compartment is formed in the receiving module body, and the seventh channel connects the eluent compartment to the extraction module.

7. A method for extracting nucleic acid, comprising steps of:
   providing an extraction cassette, wherein the extraction cassette comprises a liquid receiving module and an extraction module, the extraction module communicates with the liquid receiving module, the liquid receiving module comprises a sample compartment, an alcohol compartment, a first mixing compartment, a second mixing compartment, a first detergent compartment, a second detergent compartment and an eluent compartment;
   filling an alcohol into the alcohol compartment, filling a first detergent into the first detergent compartment, filling a second detergent into the second detergent compartment, and filling an eluent into the eluent compartment;
   filling a sample into the sample compartment;
   heating the sample inside the sample compartment;
   mixing the sample and the alcohol into a mixed liquid in the sample compartment;
   moving the mixed liquid and the sample into the extraction module from the sample compartment; and
   extracting a nucleic acid in the extraction module,
   wherein the sample compartment and the alcohol compartment are two separate compartments connected by a channel.

8. The method as claimed in claim 7, further comprising a step of:
   moving the alcohol from the alcohol compartment to the sample compartment,
   wherein the sample and the alcohol are mixed into a mixed liquid.

9. The method as claimed in claim 8, further comprising steps of:
   moving the mixed liquid into the first mixing compartment; and
   moving the mixed liquid between the first mixing compartment and the second mixing compartment repeatedly to mix the sample and the alcohol.

10. The method as claimed in claim 9, further comprising steps of:
    moving the mixed liquid into the extraction module and the nucleic acid is captured from the mixed liquid by the extraction module; and
    moving the mixed liquid into a first waste-liquid compartment of the extraction module.

11. The method as claimed in claim 10, further comprising steps of:
    moving the first detergent from the first detergent compartment to the first mixing compartment and the second mixing compartment to clean the first mixing compartment and the second mixing compartment;
    moving the first detergent to the extraction module to clean the extraction module; and
    moving the first detergent to the first waste-liquid compartment of the extraction module.

12. The method as claimed in claim 11, further comprising steps of:
    moving the second detergent from the second detergent compartment to the first mixing compartment and the second mixing compartment to clean the first mixing compartment and the second mixing compartment;
    moving the second detergent to the extraction module to clean the extraction module; and
    moving at least one portion of the second detergent to a second waste-liquid compartment of the extraction module.

13. The method as claimed in claim 12, further comprising a step of:
    moving the eluent from the eluent compartment to the extraction module to remove the nucleic acid from the extraction module.

\* \* \* \* \*